(12) United States Patent
Schacherer et al.

(10) Patent No.: US 9,345,496 B2
(45) Date of Patent: May 24, 2016

(54) TRICEPS-SPARING OLECRANON FRACTURE REPAIR DEVICE AND SYSTEM

(76) Inventors: Timothy G. Schacherer, Dallas, TX (US); Joshua S. Redstone, Dallas, TX (US)

( * ) Notice: Subject to any disclaimer, the term of this patent is extended or adjusted under 35 U.S.C. 154(b) by 390 days.

(21) Appl. No.: 13/611,763

(22) Filed: Sep. 12, 2012

(65) Prior Publication Data

US 2014/0074174 A1    Mar. 13, 2014

(51) Int. Cl.
| | | |
|---|---|---|
| *A61B 17/80* | (2006.01) | |
| *A61B 17/17* | (2006.01) | |
| *A61B 17/72* | (2006.01) | |

(52) U.S. Cl.
CPC .......... *A61B 17/1717* (2013.01); *A61B 17/1739* (2013.01); *A61B 17/7233* (2013.01); *A61B 17/808* (2013.01); *A61B 17/8061* (2013.01)

(58) Field of Classification Search
CPC ........... A61B 17/8061; A61B 17/8028; A61B 17/846; A61B 17/848
USPC .................................................. 606/286, 297
See application file for complete search history.

(56) References Cited

U.S. PATENT DOCUMENTS

| | | | | | |
|---|---|---|---|---|---|
| 2,291,413 | A | * | 7/1942 | Siebrandt ...................... 606/103 |
| 2,821,979 | A | * | 2/1958 | Cameron ........................ 606/64 |
| 3,763,855 | A | * | 10/1973 | McAtee .......................... 606/64 |
| 4,212,294 | A | * | 7/1980 | Murphy .......................... 606/64 |
| 5,006,120 | A | * | 4/1991 | Carter ............................. 606/71 |
| 5,352,229 | A | * | 10/1994 | Goble et al. .................... 606/75 |
| 5,474,553 | A | * | 12/1995 | Baumgart ............... A61B 17/80 606/309 |
| 5,772,662 | A | * | 6/1998 | Chapman et al. ............. 606/281 |
| 5,810,823 | A | * | 9/1998 | Klaue ................. A61B 17/8028 606/289 |
| 8,177,822 | B2 | * | 5/2012 | Medoff ......................... 606/297 |
| 8,439,918 | B2 | * | 5/2013 | Gelfand .......................... 606/74 |
| 8,551,143 | B2 | * | 10/2013 | Norris et al. .................. 606/280 |
| 8,668,693 | B2 | * | 3/2014 | Bernstein ........................ 606/64 |
| 2004/0116930 | A1 | * | 6/2004 | O'Driscoll et al. ............. 606/69 |
| 2006/0200127 | A1 | | 9/2006 | Ismail |
| 2007/0233113 | A1 | * | 10/2007 | Kaelblein .......... A61B 17/8061 606/71 |
| 2008/0306479 | A1 | | 12/2008 | Bernstein |
| 2009/0228009 | A1 | | 9/2009 | Duncan |
| 2010/0274293 | A1 | * | 10/2010 | Terrill ................. A61B 17/8057 606/286 |
| 2011/0160730 | A1 | * | 6/2011 | Schonhardt et al. ........... 606/71 |
| 2012/0150240 | A1 | * | 6/2012 | Medoff ......................... 606/329 |
| 2013/0237987 | A1 | * | 9/2013 | Graham ................. A61B 17/17 606/64 |
| 2013/0238035 | A1 | * | 9/2013 | Medoff ............. A61B 17/8052 606/297 |
| 2014/0330322 | A1 | * | 11/2014 | Medoff ............. A61B 17/8061 606/297 |

* cited by examiner

*Primary Examiner* — David Bates
(74) *Attorney, Agent, or Firm* — Washam PLLC; Steven H. Washam

(57) ABSTRACT

An improved olecranon fracture repair device and system. The device includes standoffs to minimize compression of a patient's triceps muscle and tendon. A buttress plate curved to approximate the olecranon process radius accepts a plurality of fixation screws is sized such that the distal end of the plate extends forward of the triceps tendon fibro-osseous junction. The system includes an installation tool having a positioning plate with a moveable member. The positioning plate serves as a stabilizing device, a medullary cavity penetration drill template, and a fixture for guiding the intramedullary rods into the cavities. The moveable member allows for removal of the tool following partial insertion of the repair device intramedullary rods.

15 Claims, 8 Drawing Sheets

TRICEPS-SPARING OLECRANON FRACTURE REPAIR DEVICE AND SYSTEM

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates to an implantable fixation device for repair of fractures of the olecranon and methods for using same.

2. Description of Related Art Including Information Disclosed Under 37 CFR 1.97 and 1.98

With regard to fractures of the olecranon requiring surgical repair, the traditional approach has been to utilize a plate/screw (see FIG. 1), tension band wiring (see FIG. 2), and/or Kirschner wire (or "K-wires" as they are known; see FIG. 3) fixation technique based upon the type and severity of the fracture. The plate/screw fixation technique is, quite simply, fixation of the fracture through the addition of a precision-designed plate made of surgical-grade alloy to the fracture site, where it is held in place using like-alloy bone screws. Use of plate/screw fixation is typically recommended for comminuted fractures and fractures that occur at or distal to the coronoid process in order to provide sufficient lateral/rotational support to the injury.

In brief, during a typical olecranon fracture repair procedure using existing fixation techniques, an incision is started posteriorly above the patients elbow, and continues distally, curving either ulnarly or radially to avoid the point of olecranon, and is continued distally towards the posterior border of the ulna to a point 3 to 4 cm distal of the fracture. An ulnarly-based incision is preferred primarily because it affords a better exposure of the ulnar nerve, which may need to be transposed anteriorly at the end of the procedure, whereas a radially based incision requires considerable undermining. With the elbow in extension such that the pull of the triceps muscle is relaxed, the fracture site then visualized by elevating the periosteum proximally with proximal fragment. If the fracture involves lateral exposure, the repair requires detachment of the aconeus muscle from the radial side of the ulna. Moreover, if the fracture involves medial exposure, the repair risks damage to the ulnar nerve. The fracture is then properly reduced and held for fixation by using one or more towel clips or K-wires while the area is prepared for fixation. For example, a properly sized plate is chosen to span the fracture and a large number of bone screws are installed. Lag screws are applied at both the proximal and distal ends in divergent positions to increase stability of the repair.

As evidenced by the above repair procedure, the plate/screw fixation technique has numerous attendant problems. For one, a large skin incision is required with the currently offered plate and screw fixation method. This results in extensive dissection of the soft tissues and large amounts of metal retained in the patient. Large plate repairs can also be felt through the thin layer of skin beneath the patient's elbow, and might also cause pain due when pressure is applied to this area or when accidental contact occurs. In fact, it is not uncommon for portions of a plate or screw heads to emerge from the patient's skin in this area.

The tension band wiring fixation technique is primarily for transverse fractures involving less than 50% of the proximal sigmoid notch, and involves the use of surgical grade wire (approximately 18 gauge) in combination with one or more lag screws, if necessary. During surgery, properly sized holes are drilled into the bone near the fracture site, through which the tension band wiring is threaded. The wire is wrapped appropriately to provide sufficient tension, thereby compressing the fracture site to facilitate healing of the fracture. This fixation technique has attendant problems as well. For example, the wire tension can be lost thereby causing the fracture to reopen.

Studies have indicated that combining a plate/screw fixation technique with a tension band improved the stability of the fixation markedly. However, the combination of these approaches results in an even greater amount of implant hardware being installed in an area of a patient's body that has relatively little cushioning due to the thin skin layer surrounding the repair. Moreover, this combination of fixation techniques merely increases the potential for problems because of each technique's aforementioned shortcomings. The invention described herein addresses many of these shortcomings and provides numerous advantages as will be understood by one of ordinary skill in the art after reading and understanding the detailed description.

BRIEF SUMMARY OF THE INVENTION

Described and claimed herein is a triceps-sparing olecranon fracture repair device, the device comprising: at least one standoff adapted to space the fracture repair device over the olecranon process to prevent compression of the patient's triceps tendon area over which the fracture repair device is to be fixated. Another embodiment of the device may include a buttress plate, the buttress plate curved to approximate the posterior radius of a patient's olecranon process, the buttress plate including a plate proximal end and a plate distal end with a length therebetween, wherein the buttress plate length positions the buttress plate distal end forward of the fibro-osseous junction of the triceps tendon when the buttress plate is fixated to the patient's olecranon process. Another embodiment of the device may include a buttress plate, the buttress plate curved to approximate the posterior radius of a patient's olecranon process, the buttress plate including a plate proximal end and a plate distal end with a length therebetween, wherein the buttress plate length positions the buttress plate distal end forward of the fibro-osseous junction of the triceps tendon when the buttress plate is fixated to the patient's olecranon process; and a plurality of fixation screw holes for fixation of the buttress plate to the olecranon process, wherein the screw holes are chamfered to allow the flush-fit of a bone screw. Another embodiment of the device may include a plurality of intramedullary rods, the rods configured to prevent rotation of the corpus ulnae relative the olecranon process. Another embodiment of the device may include two intramedullary rods, the rods configured with a divergent or convergent resting form to prevent rotation of the corpus ulnae relative the olecranon process. Another embodiment of the device may include a plurality of intramedullary rods, wherein the intramedullary rods are detachable from the fracture repair device to allow selection of rod sizes. Another embodiment of the device may include a plurality of intramedullary rods, wherein the intramedullary rods may be trimmed to a desired working length.

Also described and claimed herein is a triceps-sparing olecranon fracture repair device, the device comprising: a buttress plate, the buttress plate curved to approximate the posterior radius of a patient's olecranon process, the buttress plate including a plate proximal end and a plate distal end with a length therebetween; and at least one standoff on the buttress plate curved inner surface, the standoff adapted to space the buttress plate over the olecranon process to prevent compression of the patient's triceps tendon area over which the buttress plate is to be fixated. In another embodiment of the device the buttress plate length positions the buttress plate distal end forward of the fibro-osseous junction of the triceps tendon when the buttress plate is fixated to the patient's olecranon process. Another embodiment of the device may include a plurality of fixation screw holes for fixation of the buttress plate to the olecranon process, wherein the screw holes are chamfered to allow the flush-fit of a bone screw. Another embodiment of the device may include a plurality of intramedullary rods, each rod having a rod proximal end and a rod distal end, the rod proximal end affixed near the proximal end of the curved inner surface of the buttress plate. Another embodiment of the device may include two intramedullary rods, each rod having a rod proximal end and a rod distal end, the rod proximal end affixed near the proximal end of the curved inner surface of the buttress plate, the rods configured to prevent rotation of the corpus ulnae relative the olecranon process. Another embodiment of the device may include two intramedullary rods, each rod having a pin proximal end and a rod distal end, the rod proximal end affixed near the proximal end of the curved inner surface of the buttress plate, the rods configured with a divergent or convergent resting form to prevent rotation of the corpus ulnae relative the olecranon process. Another embodiment of the device may include a plurality of intramedullary rods, each rod having a rod proximal end and a rod distal end, the rod proximal end affixed near the proximal end of the curved inner surface of the buttress plate, wherein the intramedullary rods are detachable from the buttress plate to allow selection of pin sizes. Another embodiment of the device may include a plurality of intramedullary rods, each rod having a rod proximal end and a rod distal end, the rod proximal end affixed near the proximal end of the curved inner surface of the buttress plate, wherein the intramedullary rods may be trimmed to a desired length by the installing surgeon.

Also described and claimed herein is a triceps-sparing olecranon fracture repair system, the system comprising: an olecranon fracture repair device, the device comprising: a buttress plate, the buttress plate curved to approximate the posterior radius of a patient's olecranon process, the buttress plate including a plate proximal end and a plate distal end with a length therebetween, and a plurality of fixation screw holes for fixation of the buttress plate to the olecranon process; at least one standoff on the buttress plate curved inner surface, the standoff adapted to space the buttress plate over the olecranon process to prevent compression of the patient's triceps tendon area over which the buttress plate is fixated; and a plurality of intramedullary rods, each rod having a rod proximal end and a rod distal end, the rod proximal end affixed to the buttress plate near the proximal end of the curved inner surface; and a fracture repair device installation tool, the tool comprising: a shaft, the shaft including a shaft proximal end and a shaft distal end, the shaft proximal end including a handle for gripping; and a moveable member located on the shaft distal end, the moveable member including a positioning plate curved to approximate the posterior radius of the olecranon process, the positioning plate including a proximal end and a distal end with a length therebetween that is substantially the same as the buttress plate, the moveable member further including openings capable of accepting and supporting the plurality of intramedullary rods with the moveable member in a first position and capable of releasing the plurality of intramedullary rods with the moveable member in a second position. Another embodiment of the device may include an installation tool shaft having an axial opening that runs the entire length, the installation tool further comprising: a locking member, the locking member including an engagement feature capable of engaging the moveable member to secure the moveable member in the first position. Another embodiment of the device may include an installation tool shaft having an axial opening that runs the entire length, the installation tool further comprising: a locking member, the locking member including a shaft having a distal and a proximal end, the locking member shaft proximal end including a gripping member for applying rotational force to the locking member shaft, the locking member shaft distal end including an engagement feature capable of engaging the moveable member to secure the moveable member in the first position. In another embodiment of the device the installation tool moveable member is a hinged member. Another embodiment of the device may include at least one standoff on the curved inner surface of the installation tool positioning plate, the standoff adapted to space the positioning plate over the olecranon process to prevent compression of the patient's triceps tendon area over which the tool is to be placed.

BRIEF DESCRIPTION OF THE SEVERAL VIEWS OF THE DRAWING(S)

The present invention will be more fully understood by reference to the following detailed description of the preferred embodiments of the present invention when read in conjunction with the accompanying drawings, wherein.

Figure 10:
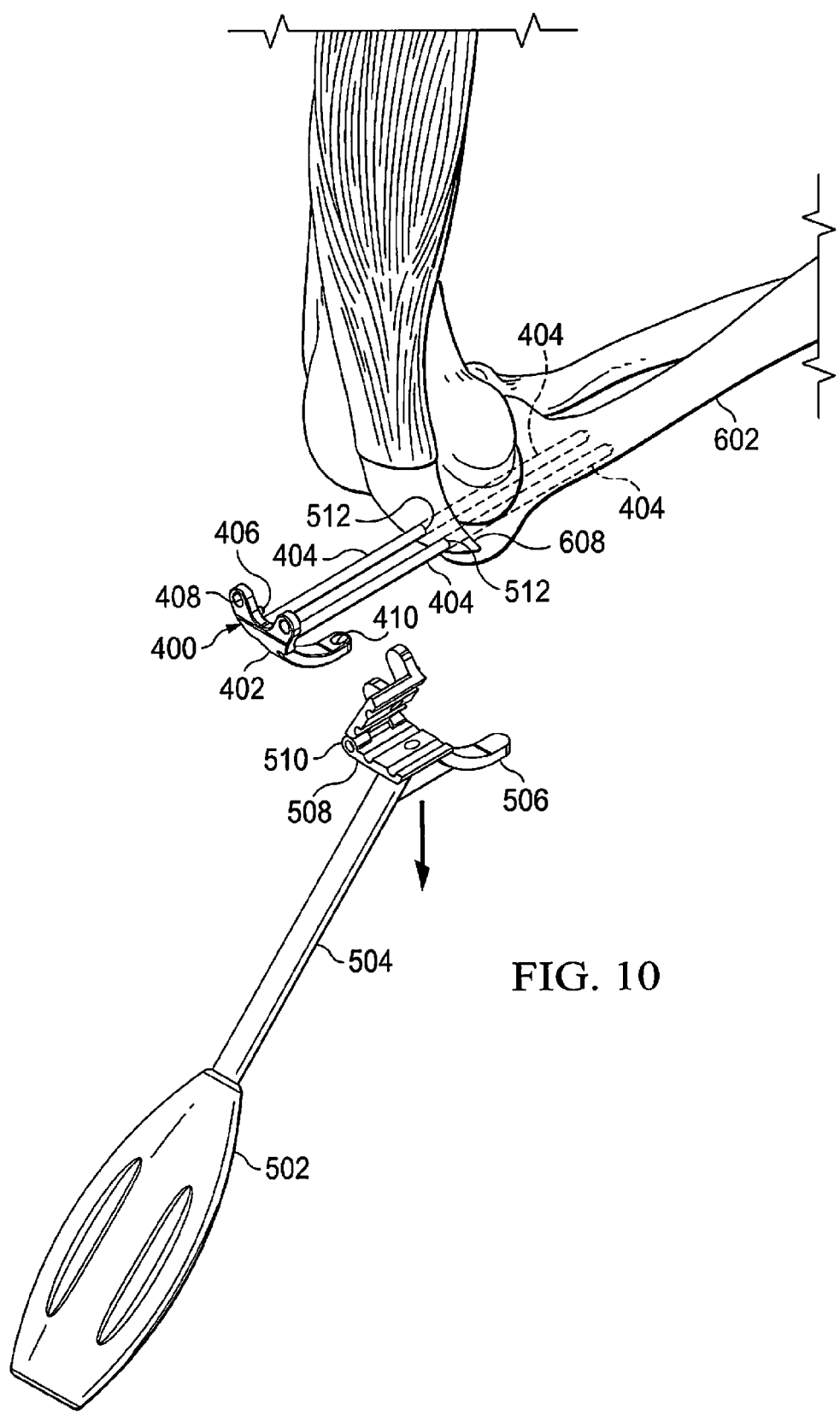
Figure 11:
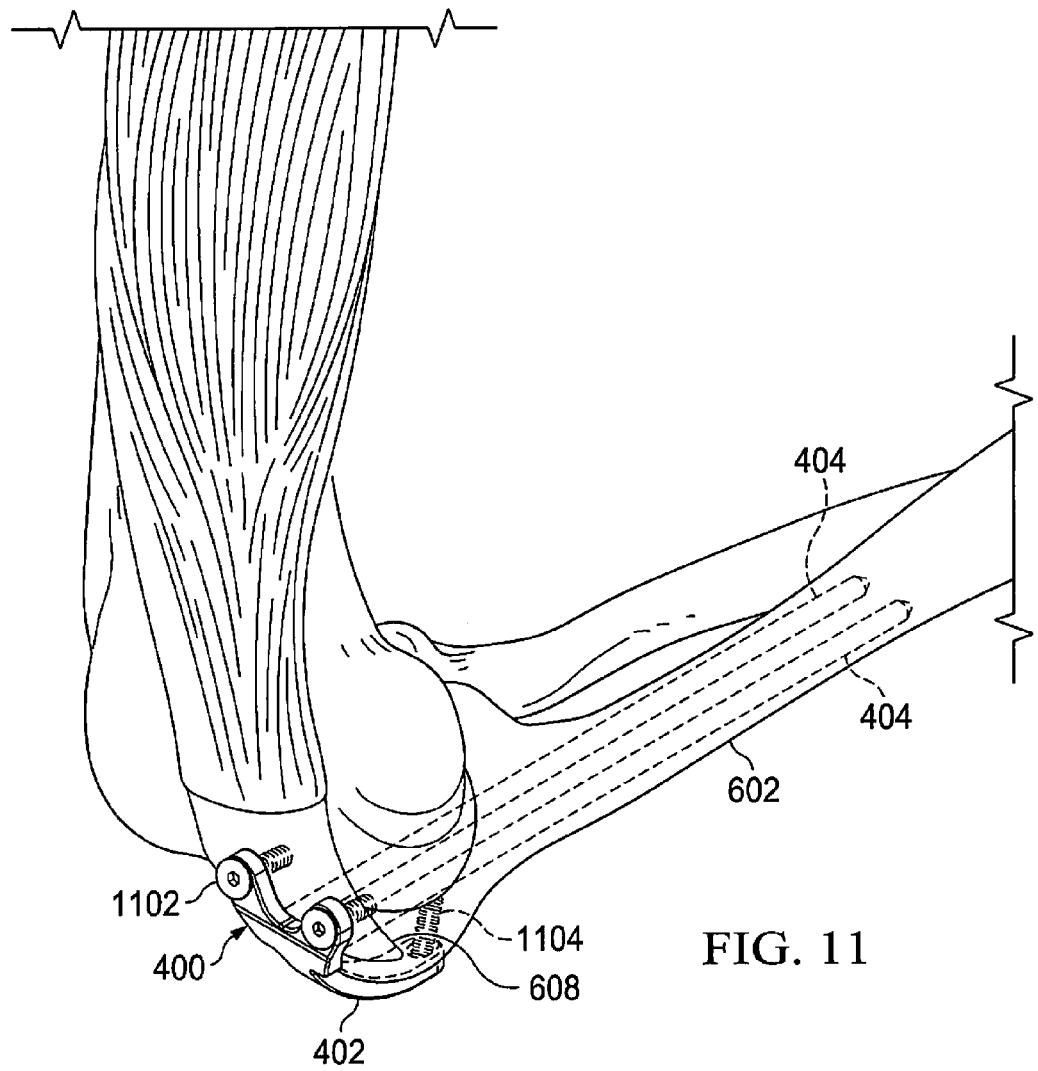

FIG. 10 is a subsequent depiction of the installation sequence wherein the installation tool embodiment is removed from the patient's olecranon and the olecranon fracture fixation device is cleared for final installation; and FIG. 11 is a subsequent depiction of the installation sequence wherein the olecranon fracture fixation device as disclosed herein is fully installed within the ulna of a patient.

The above figures are provided for the purpose of illustration and description only, and are not intended to define the limits of the disclosed invention. Use of the same reference number in multiple figures is intended to designate the same or similar parts. Furthermore, when the terms "top," "bottom," "first," "second," "upper," "lower," "height," "width," "length," "end," "side," "horizontal," "vertical," and similar terms are used herein, it should be understood that these terms have reference only to the structure shown in the drawing and are utilized only to facilitate describing the particular embodiment. The extension of the figures with respect to number, position, relationship, and dimensions of the parts to form the preferred embodiment will be explained or will be within the skill of the art after the following teachings of the present invention have been read and understood.

DETAILED DESCRIPTION OF THE INVENTION

The olecranon fracture repair device, system, and method disclosed herein reduces such fractures with a triceps-sparing approach. More specifically, the fracture repair device—as will be described in greater detail to follow—requires no removal of the triceps tendon from the periosteum of the corpus ulnae, and relatively little disruption and compression of the triceps and tendon (hence, a "triceps-sparing" approach"). The fracture repair device is installed while leaving the entire triceps tendon essentially undisturbed and intact. This device reduces the required incision size, reduces the associated dissection of the tissues and reduces the metal retained content, which reduces potential irritation. Because the size and shape of the device, the possibility of subsequent triceps tendon inflammation, rupture, tearing, or death of the tissue is reduced. Finally, the repair device produces a well-fixated fracture with reproducible results that is easier to use than any technique or fixation system currently available.

Figure 1:
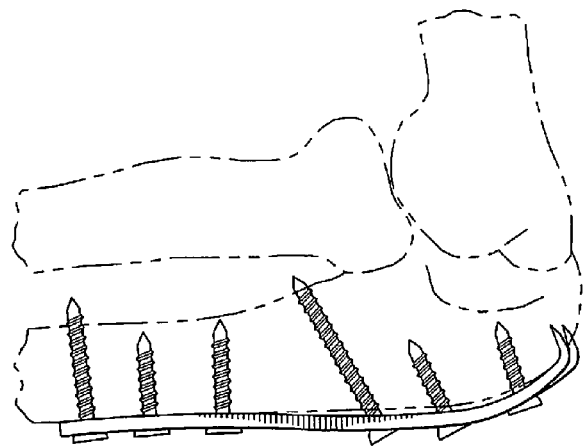
FIG. 1 is a depiction of a traditional plate and screw fixation of an olecranon fracture.
Figure 2:
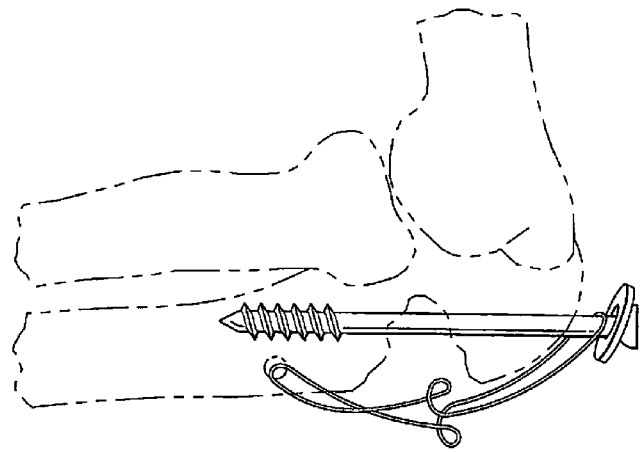
FIG. 2 is a depiction of a traditional lag screw and tension band fixation of an olecranon fracture.
Figure 3:
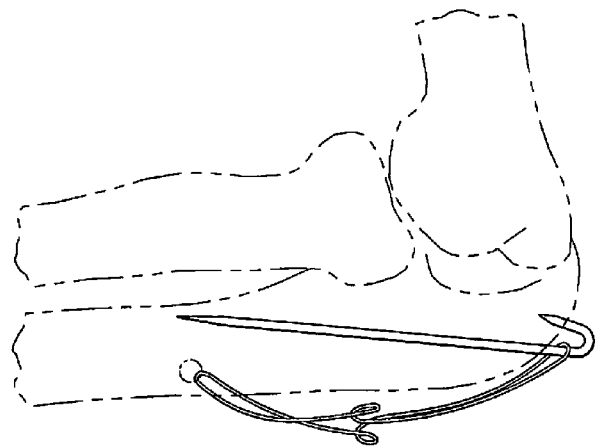
FIG. 3 is a depiction of a traditional Kirschner wire ("K-wire") fixation of an olecranon fracture.
Figure 4:
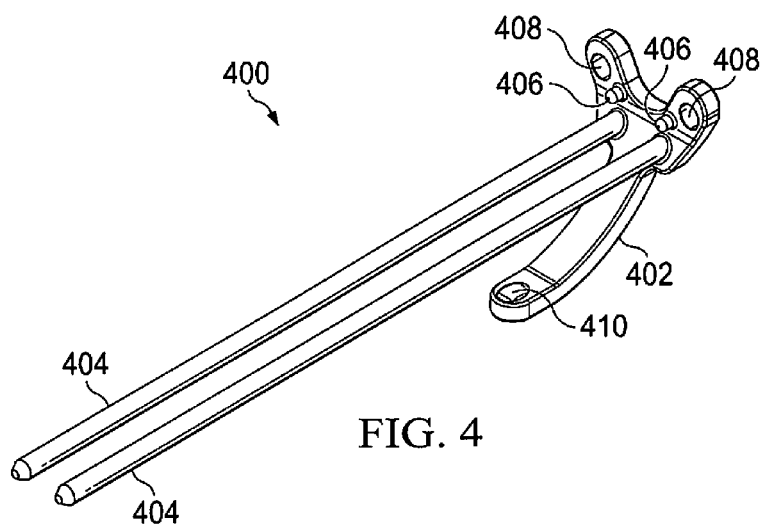
FIG. 4 is a perspective view of an embodiment of the olecranon fracture fixation device as disclosed herein.

A perspective view of an embodiment of the olecranon fracture fixation device (400) as disclosed herein is depicted in FIG. 4. As shown, the primary features of this embodiment include a buttress plate (402) with two intramedullary rods (404) and standoffs (406). A plurality of fixation screw holes (408) in the buttress plate allow fixation of a patient's olecranon fracture with the device. Given that this is a medical implant, suitable materials for construction are used. For example, the present embodiment of the device is manufactured from surgical implant grade steel, for example, surgical implant grade stainless steel, titanium, Nitinol, and the like. One of ordinary skill will appreciate that other embodiments may utilize other implant grade materials, and are within the scope of the invention claimed.

The buttress plate (402) in this embodiment is essentially a "Y" shape, with an inward curvature that approximates the curvature of the posterior radius of an olecranon process in the area in which the device is to be installed. The buttress plate (402) is approximately 1.0 mm to 3.0 mm in thickness, but may be any desired thickness selected based upon load and use requirements. A buttress plate (402) of approximately 1.5 mm in thickness is sufficiently rigid to provide fixation stability yet may flex slightly to prevent secondary fractures from occurring due to the difference in rigidity between the plate and the surrounding bone. The overall width and length of the buttress plate is determined by the size of the patient's olecranon process and the location of the attachment point of the triceps tendon. For example, a fully-grown adult will require a larger buttress plate than will a pre-teenage child. Thus, the size of the buttress plate (402) will be determined by the physical size of the patient. The overall length of the buttress plate (402) is chosen such that the lower fixation screw hole (410) is located in the periosteum of the ulna beyond the fibro-osseous junction of the triceps tendon.

Near the limits of the buttress (402) plate are fixation screw holes (408 and 410). The screw holes (408 and 410) are appropriately sized and chamfered to allow passage of a typical 2.0 mm to 5.0 mm bone screw to secure (fixate) the buttress plate (402) on the patient's olecranon process during surgery. As depicted, the end featuring two screw holes (408) is considered the proximal end of the buttress plate, while the opposite end having a single screw hole (410) is the distal end. By utilizing a sufficient chamfer, the fixation screw heads may recess within the buttress plate (402) sufficiently to minimize protrusions on the outer surface that can irritate the triceps muscle/tendon and surrounding tissue.

Immediately below the top pair of screw holes (408) near the proximal end of the present embodiment are two standoffs (406) that are approximately 0.25 mm in height. These standoffs (406) emanate from the buttress plate (402) perpendicular to the inner curved surface. The standoffs (406) serve to space the device from the olecranon in order to prevent excessive compression of the triceps muscle and tendon during device fixation, thereby affording adequate blood flow to these tissues to ensure rapid healing and normal functioning. Further, the standoffs (406) penetrate the muscle and tendon tissue, thereby providing some positional stability for the device during the fixation process.

The buttress plate (402) from the proximal end to the distal end measures approximately 3.0 cm in length. However, as previously stated, this length is determined largely by the physical size of the patient and more specifically by the distance from the posterior of the olecranon process at the point that is substantially in line with the axis of the corpus ulnae to the beginning of the attachment point of the triceps tendon to the ulna. The width of the buttress plate (402) near the distal end (single fixation screw hole) is approximately 2.0 mm, while the proximal end is approximately 1.5 cm at its widest point. The overall width of the buttress plate (402) is maintained as large as possible for fixation stability, yet sufficiently narrow to provide a margin such that the outermost fixation screws are located within the outer edges of the triceps tendon tissue.

This embodiment also utilizes two intramedullary rods (404) that are approximately 1.5 mm in diameter (0.62 in) and approximately 7.5 cm in length. The diameter of the rods (404) is chosen to provide the desired tensile and shear strength for a repair. The distal end of the rods (404) includes a taper to aid in insertion of the rods into corresponding passages to be drilled within the medullary canal of the bone under repair. The proximal end of the rods (404) is affixed to the inner curved surface near the proximal end of the buttress plate (402), which is also near the standoffs (406). The intramedullary rods (404) in the present embodiment are formed to the buttress plate (402) during manufacture and may be provided in different lengths. In another embodiment the intramedullary rods are welded or swedged to the buttress plate. The overall length of the intramedullary rods is determined, once again, by the physical size of the patient. In another embodiment the intramedullary rods (404) are attached to the buttress plate (402) using threads or a similar fastener to allow the rods (404) to be changed. In yet another embodiment the rods (404) may be trimmed using a cutting tool. Thus, rods of different length (and/or diameter) may be chosen and installed (or trimmed) prior to fixation of the device during surgery.

The present embodiment utilizes two, parallel intramedullary rods (404). One of the benefits of having two rods over a single rod is that smaller multiple holes may be drilled within the medullary cavity, leaving more of the core cavity tissue intact. Moreover, use of two rods (404) provides for added stability to prevent rotation of the corpus ulnae relative to the olecranon process along the fracture lines. Finally, use of two parallel rods (404) provides a gap therebetween through which the lower fixation screw may pass upon insertion, therefore allowing use of a longer screw in this position. Other embodiments may utilize more than two rods depending on the bone diameter and type of fracture.

Although the embodiment depicts parallel intramedullary rods (404), other embodiments utilize a resting arrangement for the rods that is not parallel. For example, another embodiment of the device provides intramedullary rods that are divergent or convergent in resting form. When the divergent intramedullary rods are inserted within the patient's medullary cavity, a form of preload is provided to the ulna that helps to resist rotation of the fractured bone. In another embodiment with three intramedullary rods, the rods are in a skew-divergent resting form, which provides additional such preload for dynamically stabilizing a patient's fracture.

Although a "Y" shaped buttress plate is depicted, other embodiments may utilize different shapes. For example, another embodiment utilizes an "H" shaped buttress plate with a similar olecranon process curve and having holes near the ends for accepting four fixation screws. Standoffs also emanate from the legs of the buttress plate, while the crossbar of the "H" shape also supports location of the intramedullary rods. An "H" shape may be preferable on patients with more complex fractures that would benefit from an additional fixation screw near the lower portion of the olecranon process. Further, another embodiment may utilize a ladder-type configuration (essentially a modified "H" shape having multiple crossbars) for the buttress plate. The multiple crossbars allow support for additional (multiple) intramedullary rods.

Figure 5:
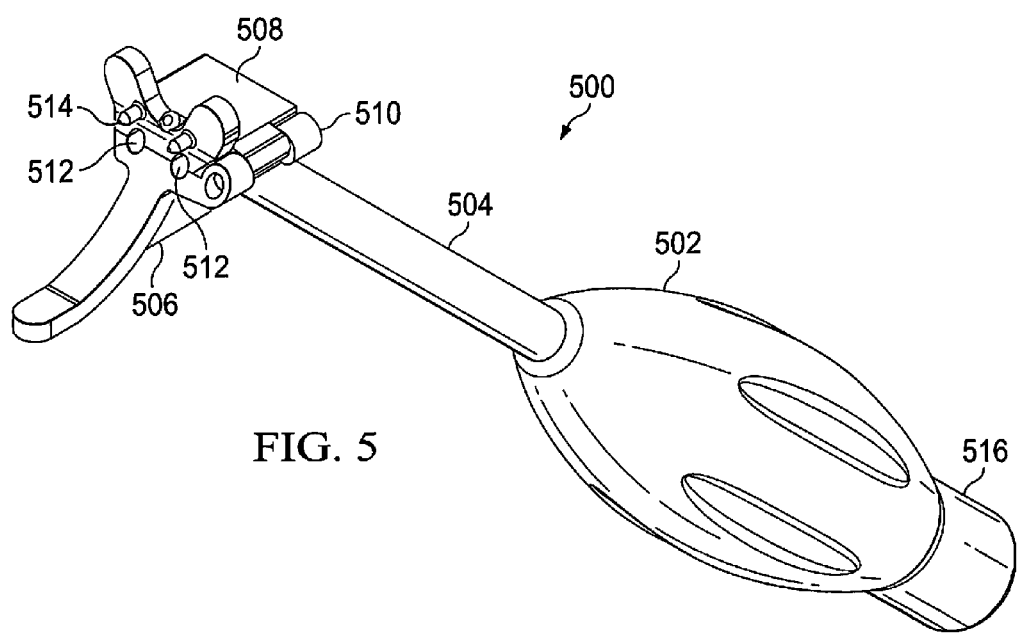
FIG. 5 is a perspective view of an embodiment of the olecranon fracture fixation device installation tool as disclosed herein.

A perspective view of an embodiment of the triceps-sparing olecranon fracture fixation device installation tool (500) as disclosed herein is depicted in FIG. 5. The installation tool (500) serves as a medullary cavity drill template and a support fixture for installation of the fracture repair device rods (404). As shown, the installation tool (500) includes a shaft (504) with a proximal and a distal end. The proximal end of the shaft includes a handle (502) for gripping by a surgeon, with a working head on the distal end.

In this embodiment the working head of the installation tool (500) includes a positioning plate (506) similar to the buttress plate of the fracture fixation device (400). As shown, the positioning plate (506) is similar in shape and includes a curved inner surface that, like the buttress plate (402), approximates the curvature of the olecranon process. Although the tool (500) depicted herein features a positioning plate (506) with substantially a "Y" configuration, other embodiments having an "H" or modified "H" with additional crossbars may be used to match the chosen fracture fixation device buttress plate shape.

The positioning plate (506) proximal end is attached to the handle (504) and includes a movable member (508). In this embodiment the movable member (508) is hinged (510) to allow for rotation of the movable member (508) along the hinge axis such that it rotates away from the shaft (504) as shown. As depicted, the movable member is shown in a first (closed) position. A locking member is also provided to maintain the movable member in this position during operation of the tool. Although a hinge with a pin is depicted, other embodiments may utilize no hinge whatsoever and may merely allow the movable member to be removed completely when not held or retained in the first position.

Figure 8:
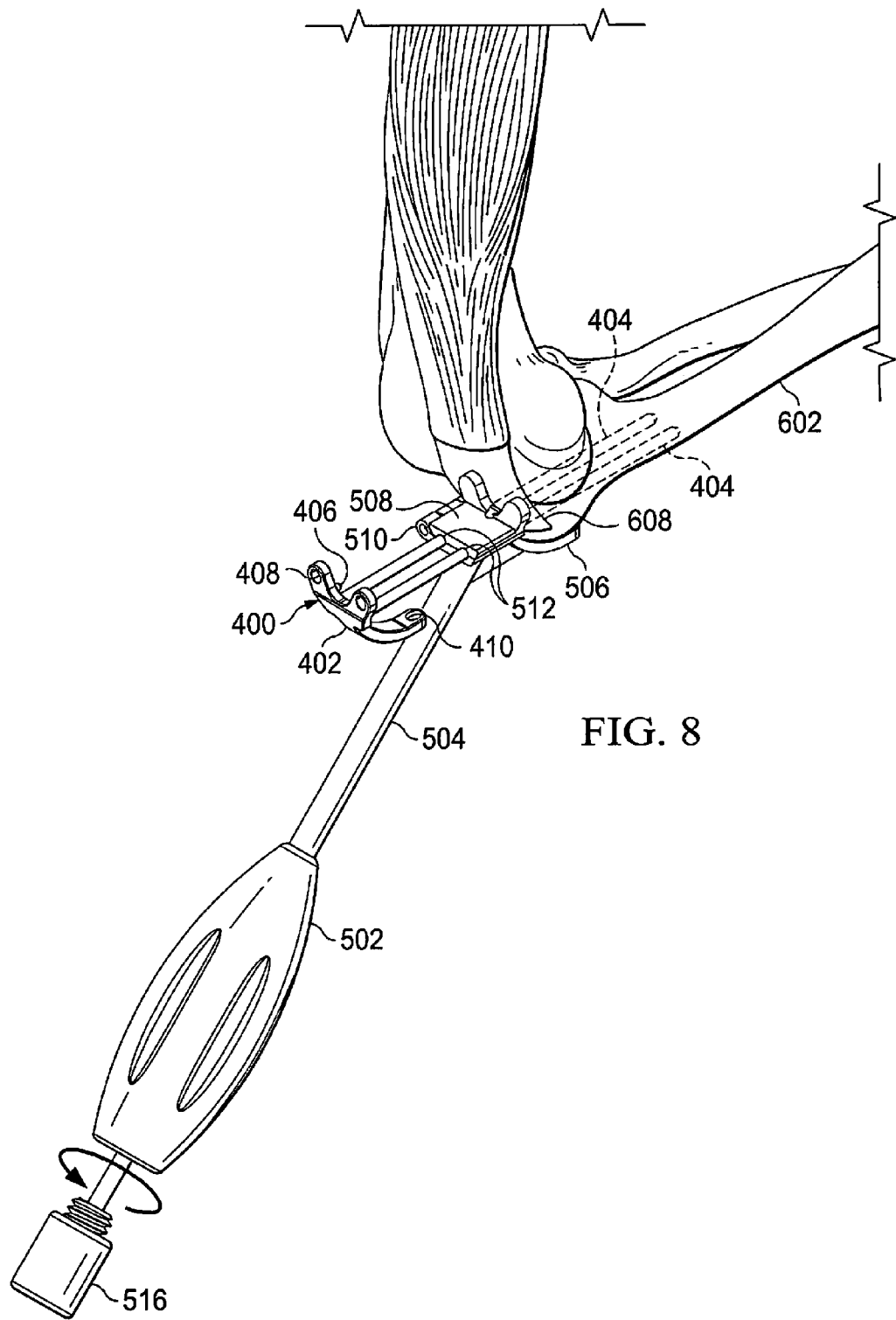
FIG. 8 is a subsequent depiction of the installation sequence wherein the installation tool embodiment is unlocked for removal from the patient.
Figure 9:
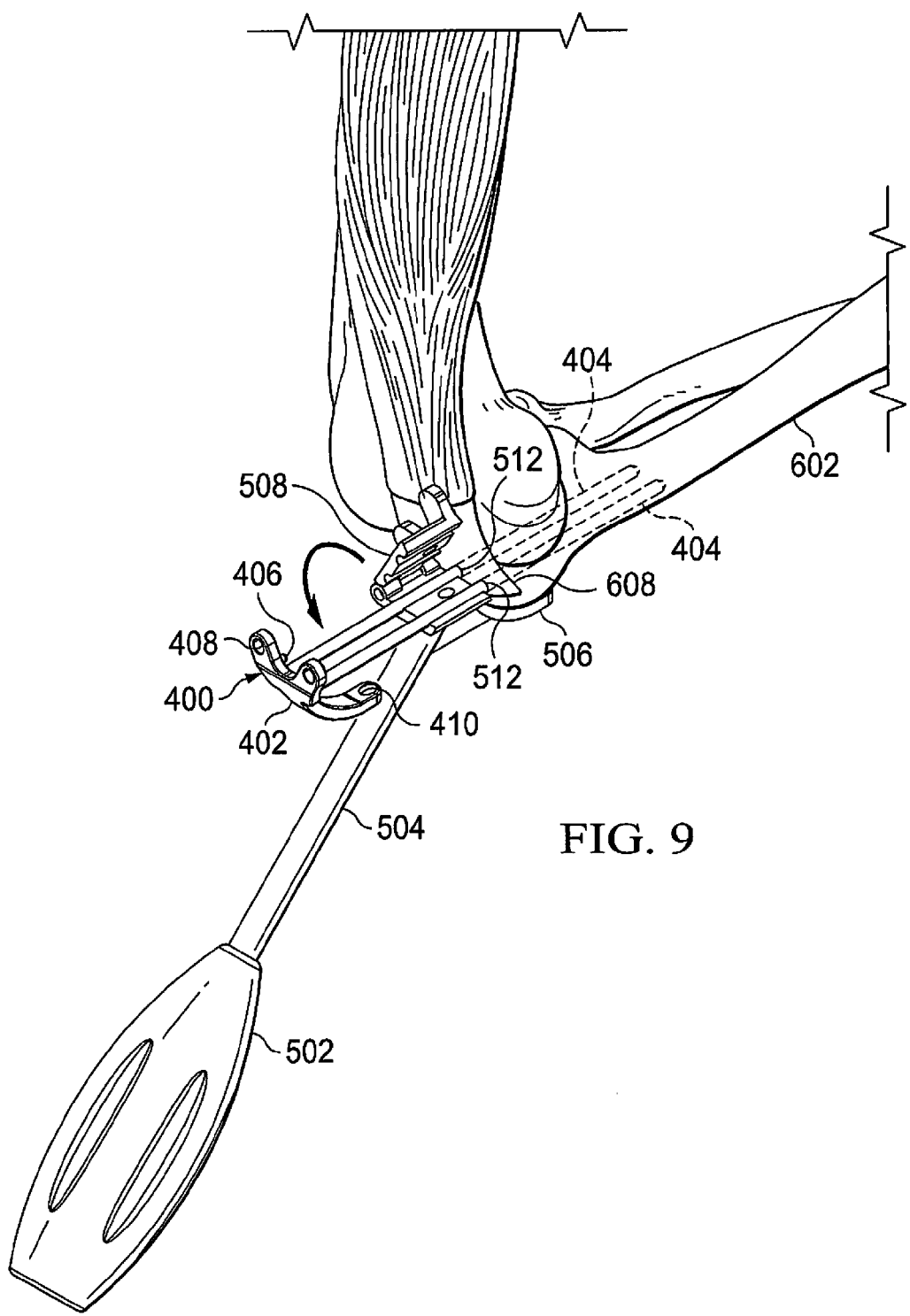
FIG. 9 is a subsequent depiction of the installation sequence wherein the installation tool embodiment head portion is laid back upon its hinge to effect tool removal.

The locking member of the embodiment comprises a gripping member (516) attached to the proximal end of a shaft that extends the length of the tool shaft (504) and is capable of rotating and moving within the tool shaft (504). The distal end of the locking member includes an engagement feature that allows the locking member to physically engage the movable member (508) to retain it in the first (closed) position. The movable member (508) may be subsequently disengaged by rotating the locking member handle (516) a sufficient number of turns. The engagement feature of the present embodiment is a threaded section that engages a mating threaded section on the movable member face. However, in another embodiment the engagement member is a partial turn slot/taper arrangement that allows the engagement/disengagement to occur with less than a full rotation of the locking member handle (516). FIGS. 8 and 9 depict use of the locking member (516) and subsequent rotation of the movable member (508).

Referring once more to FIG. 5, in the space between the faces of the moveable member (508) and the portion of the positioning plate (506) attached to the handle are two openings (512) that run parallel to the hinge (510) axis and extend the entire length of the faces. These openings (512) are sized such that the diameter and spacing allow passage therethrough of the intramedullary rods (404) of the fracture repair device (400) to provide support during installation. Also, prior to the insertion of the intramedullary rods (404), the openings may be used as a drill guide (or template) for the formation of the medullary cavity penetrations. The surgeon performing the fracture reduction/fixation may engage the damaged olecranon process with the positioning plate (506) to during the repair procedure. Standoffs (514) are also provided to prevent excessive compression of the triceps tendon during use, to mark the triceps tendon tissue where the fracture repair device (400) standoffs (406) will penetrate, and to serve to stabilize the positioning plate (506) on the patient's olecranon and to prevent slippage while drilling the intramedullary rod penetrations.

Figure 6:
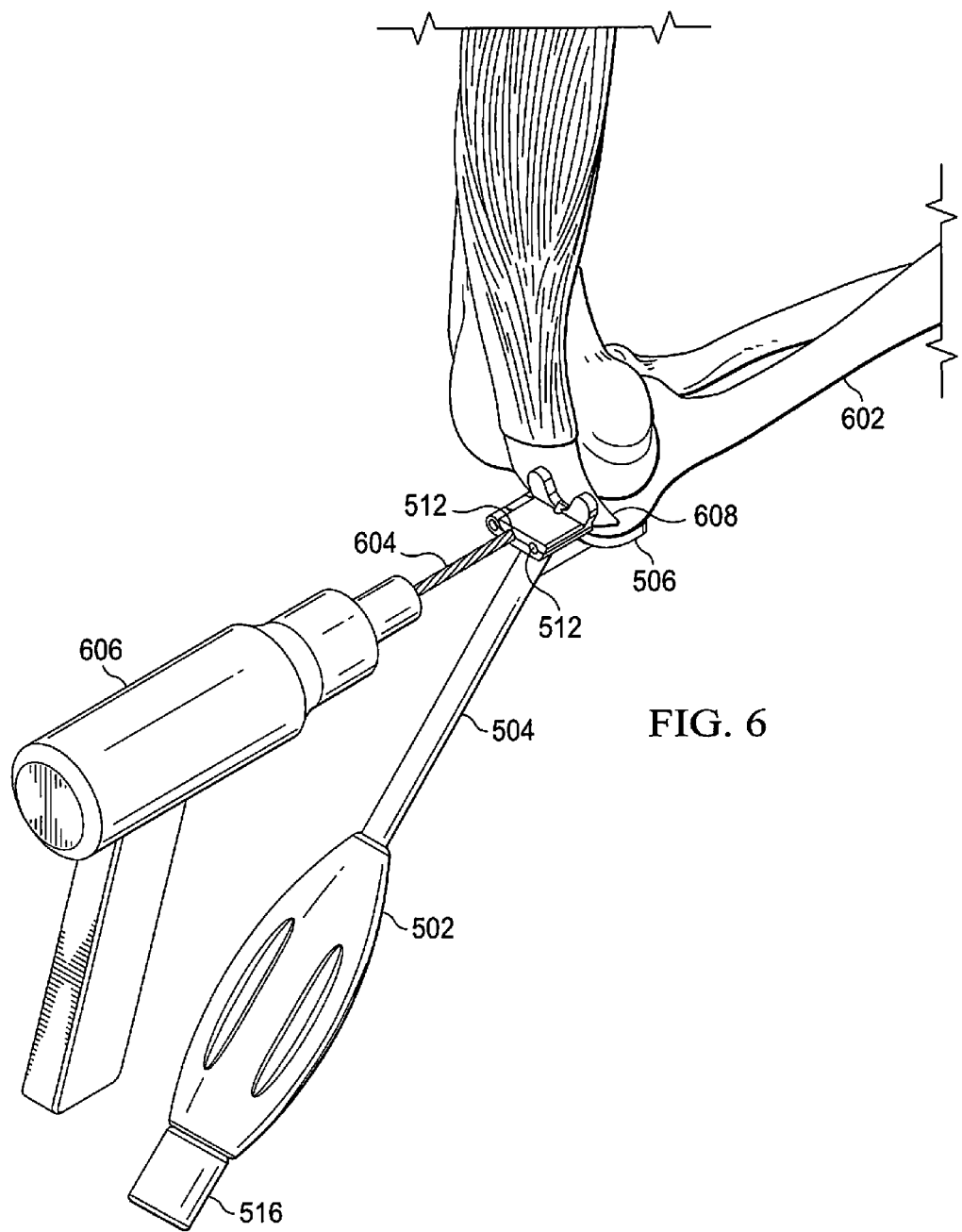
FIG. 6 is a depiction of a patient's arm being prepped for installation of the olecranon fracture fixation device by using the installation tool embodiment.
Figure 7:
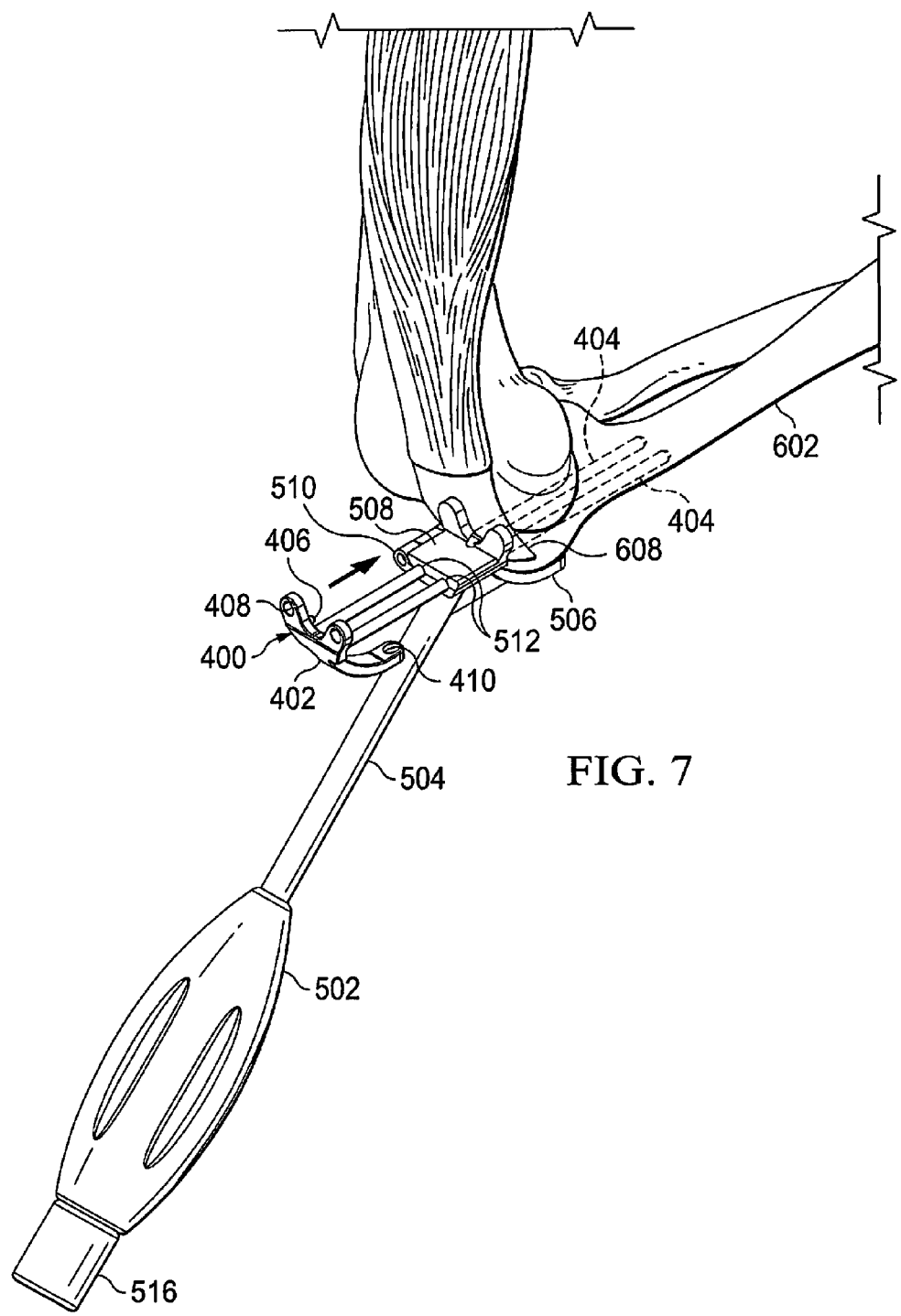
FIG. 7 is a subsequent depiction of the installation sequence of the olecranon fracture fixation device embodiment using the installation tool embodiment.

The olecranon fracture repair device and installation tool may be utilized as follows. While it is possible to implant the novel fracture repair device disclosed herein using conventional methods, the likewise novel installation tool disclosed herein provides added advantages and its use may be preferred. A depiction of a patient's arm being prepped for installation of the olecranon fracture fixation device by using the installation tool embodiment is depicted in FIG. 6. After exposing the elbow the fracture may be reduced temporarily by standard means such as clamps, towel clips, or the like. Next, a fracture repair device (400) is chosen such that the length of the buttress plate (402) places the lowermost fixation screw (410) forward of the fibro-osseous junction (608). A corresponding installation tool (500) is also chosen. The installation tool positioning plate (506) is then positioned over the triceps tendon on the olecranon process such that the installation tool openings (512) approximately align with the medullary cavity of the ulna (602), and his held firmly in place. At this point the moveable head of the tool is locked in the first position by the locking member (516). A surgical drill (606) and an appropriately sized drill bit (604) may then be used to drill the medullary cavity penetrations using the openings (512) as a template. The surgeon drills the penetrations through the triceps tendon and olecranon process and into the medullary cavity to the appropriate depth based on the needs of the repair, and the drill bit is removed. As depicted in FIG. 7, with the surgeon still holding the installation tool in place, the repair device (400) is partially implanted by passing the intramedullary rods (404) through the tool openings (512), and partially inserting the rods (404) into the medullary cavity penetrations. Once the repair device (400) is partially inserted, the installation tool may be removed from the area as depicted in FIGS. 8 and 9.

As shown in FIG. 8, the surgeon first unlocks the installation tool moveable member (508) by rotating the locking member gripping member (516) and pulling it slightly or completely out of the tool shaft (504). Once the moveable member (508) is unlocked as depicted in FIG. 9, the moveable member is rotated so an unlocked second position (open) thereby exposing the intramedullary rods (404). The installation tool positioning plate (506) may then be removed from the repair area with minimal disturbance of the repair device (400). Once the installation tool is clear of the repair device (400), the repair device is then fully implanted and the fracture permanently reduced by firmly engaging the repair device buttress plate (402) with the olecranon process and installing the requisite fixation screws (1102). Standoffs (406) on the repair device prevent undue compression of the triceps muscle and tendon thereby preventing loss of blood flow to these tissues.

One of ordinary skill in the art will appreciate that most of the device implant steps described herein are commonly practiced and understood. For example, the surgical procedures necessary to expose the olecranon process and manipulate the surrounding structure are relatively well known in the art. Moreover, selection and implantation of fixation screws is commonly performed.

The invention may be embodied in other specific forms without departing from the spirit or essential characteristics thereof. The present embodiments are therefore to be considered in all respects as illustrative and not restrictive. Accordingly, the scope of the invention is established by the appended claims rather than by the foregoing description. All changes which come within the meaning and range of equivalency of the claims are therefore intended to be embraced therein. Further, the recitation of method steps does not denote a particular sequence for execution of the steps. Such method steps may therefore be performed in a sequence other than that recited unless the particular claim expressly states otherwise.

We claim:

1. A triceps-sparing olecranon fracture repair device, the device comprising:
    a buttress plate having an inner surface and an outer surface comprising:
        at least one fixation screw hole having an axis passing from the outer surface to the inner surface;
    a plurality of intramedullary rods indivisibly affixed to the inner surface, the intramedullary rods configured to prevent rotation of a patient's corpus ulnae relative to the patient's olecranon process when the intramedullary rods are inserted within the intramedullary space of the patient's bone and the buttress plate is fixated over the patient's olecranon process; and
    at least one standoff indivisibly affixed to the inner surface and extending therefrom, the standoff having an end configured to contact bone and adapted to space the buttress plate inner surface over the patient's distal triceps tendon on a posterior radius of the patient's olecranon process to prevent compression by the buttress plate of the patient's triceps tendon when the intramedullary rods are inserted within the intramedullary space of the patient's bone and the buttress plate is fixated by at least one fixation screw through the at least one fixation screw hole.

2. The device of claim 1, wherein the buttress plate is curved to approximate the posterior radius of the patient's olecranon process, the buttress plate including a plate proximal end and a plate distal end with a length therebetween, wherein the buttress plate length positions the buttress plate distal end forward of the fibro-osseous junction of the triceps tendon when the buttress plate is fixated to the patient's olecranon process.

3. The device of claim 1, wherein the buttress plate is curved to approximate the posterior radius of the patient's olecranon process, the buttress plate including a plate proximal end and a plate distal end with a length therebetween, wherein the buttress plate length positions the buttress plate distal end forward of the fibro-osseous junction of the triceps tendon when the buttress plate is fixated to the patient's olecranon process, the buttress plate further comprising:
    a plurality of fixation screw holes for fixation of the buttress plate to the olecranon process, wherein the screw holes are chamfered to allow the flush-fit of a bone screw.

4. The device of claim 1, wherein the intramedullary rods are configured with a divergent or convergent resting form.

5. The device of claim 1, wherein the intramedullary rods may be trimmed to a desired working length.

6. A triceps-sparing olecranon fracture repair device, the device comprising:
    a buttress plate, the buttress plate having an inner surface and an outer surface, the inner surface curved to approximate a posterior radius of a patient's olecranon process, the buttress plate including a plate proximal end and a plate distal end with a length therebetween;
    at least one fixation screw hole having an axis passing from the outer surface to the inner surface;
    a plurality of intramedullary rods, each rod having a rod proximal end and a rod distal end, the rod proximal end indivisibly affixed near the proximal end of the curved inner surface of the buttress plate and configured to prevent rotation of the patient's corpus ulnae relative to the patient's olecranon process when the intramedullary rods are inserted within the intramedullary space of the patient's bone and the buttress plate is fixated over the patient's olecranon process; and
    at least one standoff indivisibly affixed to the inner surface and extending therefrom, the standoff having an end configured to contact bone and adapted to space the buttress plate inner surface over the distal triceps tendon on the posterior radius of the patient's olecranon process to prevent compression of the patient's distal triceps tendon when the intramedullary rods are inserted within the intramedullary space of the patient's bone and the buttress plate is fixated by at least one fixation screw through the at least one fixation screw hole.

7. The device of claim 6, wherein the buttress plate length positions the buttress plate distal end forward of the patient's fibro-osseous junction of the triceps tendon when the buttress plate is fixated to the patient's olecranon process.

8. The device of claim 6, the buttress plate further comprising:
    a plurality of fixation screw holes for fixation of the buttress plate to the olecranon process, wherein the screw holes are chamfered to allow the flush-fit of a bone screw.

9. The device of claim 6, wherein the rods are configured with a divergent or convergent resting form.

10. The device of claim 6, wherein the intramedullary rods may be trimmed to a desired length by the installing surgeon.

11. A triceps-sparing olecranon fracture repair system, the system comprising:
- an olecranon fracture repair device, the device comprising:
- a buttress plate, the buttress plate having an inner surface and an outer surface, the inner surface curved to approximate a patient's olecranon process posterior radius, the buttress plate including a plate proximal end and a plate distal end with a length therebetween, and a plurality of fixation screw holes for fixation of the buttress plate to the olecranon process;
- at least one standoff on the buttress plate curved inner surface, the standoff adapted to space the buttress plate over the distal triceps tendon on the posterior radius of the patient's olecranon process to prevent compression of the patient's distal triceps tendon in the area over which the buttress plate is fixated; and
- a plurality of intramedullary rods, each rod having a rod proximal end and a rod distal end, the rod proximal end affixed to the buttress plate near the proximal end of the curved inner surface and configured to prevent rotation of the patient's corpus ulnae relative to the patient's olecranon process; and
- a fracture repair device installation tool, the tool comprising:
- a shaft, the shaft including a shaft proximal end and a shaft distal end, the shaft proximal end including a handle for gripping; and
- a moveable member located on the shaft distal end with a hinge therebetween, the moveable member including a first portion of a positioning plate, with a second portion of the positioning plate included on the shaft distal end, the first and second portions forming a positioning plate curved to approximate the posterior radius of the olecranon process, the positioning plate including a proximal end and a distal end with a curve therebetween that is substantially the same as the buttress plate, the moveable member further including openings formed between the moveable member and the distal end, the openings capable of accepting and supporting the plurality of intramedullary rods with the moveable member in a first position and capable of releasing the plurality of intramedullary rods with the moveable member in a second position, wherein the positioning plate engages the posterior radius of the olecranon process to allow the moveable member openings to serve as drill guides for forming penetrations in the olecranon process to allow insertion of the intramedullary rods.

12. The system of claim 11, the installation tool shaft having an axial opening that runs the entire length, the installation tool further comprising:
- a locking member, the locking member including an engagement feature capable of engaging the moveable member to secure the moveable member in the first position.

13. The system of claim 11, the installation tool shaft having an axial opening that runs the entire length, the installation tool further comprising:
- a locking member, the locking member including a shaft having a distal and a proximal end, the locking member shaft proximal end including a gripping member for applying rotational force to the locking member shaft, the locking member shaft distal end including an engagement feature capable of engaging the moveable member to secure the moveable member in the first position.

14. The system of claim 11, wherein the installation tool moveable member is a hinged member.

15. The system of claim 11, the system further comprising:
- at least one standoff on the curved inner surface of the installation tool positioning plate, the standoff adapted to space the positioning plate over the olecranon process to prevent compression of the patient's triceps tendon area over which the tool is to be placed.

\* \* \* \* \*